United States Patent [19]

Goldstein et al.

[11] 4,031,090

[45] June 21, 1977

[54] STABILIZED ISOCYANURATE

[75] Inventors: David Goldstein, East Brunswick; William Henry Kibbel, Jr., Pennington; Roger C. Hollenbach, Kendall Park, all of N.J.

[73] Assignee: FMC Corporation, Philadelphia, Pa.

[22] Filed: Jan. 23, 1976

[21] Appl. No.: 651,942

[52] U.S. Cl. .................... 260/248 C; 260/248 A
[51] Int. Cl.² ............. C07D 251/36; C07D 251/32
[58] Field of Search .................. 260/248 C, 248 A

[56] References Cited

UNITED STATES PATENTS 3,853,867  12/1974  Berkowitz .................... 260/248

Primary Examiner—John M. Ford
Attorney, Agent, or Firm—Robert D. Jackson; Frank Ianno

[57] ABSTRACT

Process for preparing a granulated, stabilized alkali metal dichloroisocyanurate by mixing 10–70% of an alkali metal dichloroisocyanurate with 25–75% of cyanuric acid or alkali metal salt thereof, and 5–50% of an inorganic salt, having a pH in water of at least 9, wherein the ingredients are a homogeneous powder and are compacted under pressure, and the compacts crushed to provide a −10 +70 mesh product fraction.

2 Claims, No Drawings

STABILIZED ISOCYANURATE

This invention relates to the preparation of granulated, stabilized dichloroisocyanuric acid salts having improved dissolution properties.

The chlorinated cyanuric acids are well known in the art as a source of active chlorine and have been widely used to provide active chlorine in water supplies, to prevent the growth of pathogenic bacteria in swimming pools, and in detergent and sanitizing compositions. In particular, the alkali metal salts of dichloroisocyanuric acid have been accepted as a convenient means for supplying active chlorine, because of the good stability which they possess under normal handling conditions. The decomposition temperature of these salts is sufficiently high to preclude reaching their decomposition point under normal handling and storage conditions.

Despite the fact that the salts of dichloroisocyanuric acid are generally stable, they display an extraordinary type of decomposition which is most serious. If any portion of the bulk mass of the salt is exposed to a source of intense heat (e.g., an unextinguished match or cigarette butt), there commences a creeping self-sustaining, thermally-initiated decomposition which ultimately decomposes the entire quantity of salt. The effect of such decomposition is the complete destruction of the ability of the dichloroisocyanuric acid salts to yield active chlorine, and consequently the primary chemical utility of the salt is lost.

According to U.S. Pat. No. 3,145,206 issued to Fuchs et al, such decomposition can be inhibited by mixing dry salts of dichloroisocyanuric acid with up to about 25% of dichloroisocyanuric acid or cyanuric acid. However, when cyanuric acid or an alkali metal salt thereof is used as the stabilizer at concentrations higher than this patent discloses, the resultant composition is prone to chemically-initiated decomposition. This latter type of breakdown is manifested by the evolution of chloramines, especially nitrogen trichloride, a highly reactive and even explosive compound.

Copending U.S. patent application Ser. No. 357,481, filed May 4, 1973, now U.S. Pat. No. 3,853,867, discloses that the chloramine-liberating chemical decomposition of dichloroisocyanuric acid salts which are admixed with cyanuric acid or alkali metal salts thereof (to stabilize against thermal decomposition) may be avoided by formulating such mixtures to contain 5–50% of an inorganic salt which exhibits in aqueous media a pH of at least 9, preferably 9–13.

Mixtures of cyanuric acid or its alkali metal salts with alkali metal dichloroisocyanurates which are stabilized against both thermal decomposition and chemical decomposition and are suitable for water treatment comprise 10–70% of an alkali metal dichloroisocyanurate, 25–75% of cyanuric acid or the alkali metal salt thereof, and 5–50% of an inorganic salt having a pH of at least 9 in aqueous media.

Since cyanuric acid or its alkali metal salts are added to swimming pools or other large bodies of water in combination with alkali metal dichloroisocyanurates to retard chlorine dissipation, such a stabilized dry blend of these ingredients greatly facilitates their shipping and handling.

Mixtures of cyanuric acid or its alkali metal salts with alkali metal dichloroisocyanurates which are particularly well adapted for treatment of freshly filled swimming pools or other large bodies of water will provide ratios of cyanuric acid:available chlorine ranging from 25:5 to 35:25. A preferred combination within these ranges will comprise 25 parts of cyanuric acid:10 parts of available chlorine.

This preferred combination will be provided, for example, by a composition comprising 43% cyanuric acid, 47.5% sodium dichlorisocyanurate, and 9.1% sodium carbonate as the alkaline salt to stabilize against the chloramine-liberating chemical decomposition of the sodium dichloroisocyanurate.

When sodium dichloroisocyanurte dihydrate is used as a source of available chlorine, the preferred proportions (25:10) will be provided in a stabilized mixture comprising 41.8% cyanuric acid, 49.1% sodium dichlorocyanurate dihydrate, and 9.1% sodium carbonate.

The cyanuric acid in such mixtures dissolved more slowly than the other components when the mixture is placed in water. When the mixtures are formulated with granular materials, the slow dissolution of cyanuric acid delays the onset of active chlorine stabilization in solution, especially when the slowlydissolving granules of cyanuric acid settle in dead spots where circulation of the water in the system is poor. In a swimming pool the slowly-dissolving granules will give the impression of an insoluble residue, and further, the particles can build up on the pool filter and be lost in the sewer if filter backwashing is effected too promptly.

Formulation with powdered raw materials in order to improve the dissolution characteristics presents the well-known disadvantage of finely powdered mixtures, such as segregation in the package and dusting during handling and use, with resultant unpleasantness for the user.

It has now been discovered that powdered cyanuric acid or its alkali metal salts, a powdered alkali metal salt of dichloroisocyanuric acid and a powdered inorganic salt having a pH of at least 9 in aqueous solution may be intimately mixed together in desired proportions and then compacted to obtain a homogeneous compact which can be crushed and sized to provide a granular product dissolving substantially more rapidly than the simple mechanical mixtures of granular raw materials previously described. The disadvantages of a mixed granular product are overcome, and the drawbacks of a mixture of powdered raw materials are avoided.

The process of this invention may be practiced by mixing powdered cyanuric acid or its alkali metal salts, a powdered alkali metal salt of dichloroisocyanuric acid and a powdered alkaline inorganic salt (having a pH of at least 9 in aqueous solution) in any type of mixing equipment such as a ribbon blender, a twin-shell blender, or cone blender which is capable of providing an intimate, homogeneous mixture of the ingredients. Compaction of the intimate, homogeneous mixture of powdered ingredients may be carried out in a tableting press, on a compacting roll, in a briquetting machine or other suitable means known to the art. The compacts were crushed in an impact mill to obtain granules of −10+70 (U.S. Standard Sieves), recycling oversize to a grinding mill, and undersize to the compactor. The recycled oversize, after grinding, is then blended together with the powdered feed constituents in the aforementioned mixing equipment.

The practice of the invention is exemplified in the following Examples.

EXAMPLE I

Powder blends of about 200 g were made in a Paterson-Kelly Twin Shell Blender by mixing ingredients for 15 minutes in the following proportions: 43.4% of cyanuric acid, 47.5% of sodium dicloroisocyanurate, and 9.1% of sodium carbonate. The cyanuric acid showed the following particle size analysis (by Bahco subscreen analyzer):

| Particle Size, Microns | Cumulative % Greater Than |
| --- | --- |
| 149 | 1.2 |
| 34 | 43.2 |
| 27 | 53.4 |
| 14 | 71.7 |
| 10 | 80.6 |
| 5 | 89.7 |
| 3 | 93.6 |
| 2 | 97.0 |
| <2 | 3.0 |

The sodium dichloroisocyanurate was 0.5% maximum on 30 mesh (U.S. Standard Sieve) and 5.0% maximum on 200 mesh (U.S. Standard Sieve). The sodium carbonate was Solvay light ash, 0% on 40 mesh and 20% on 100 mesh.

Dissolution studies were made in a 1,400 ml. beaker containing 1,000 ml of water at 25.5°–26.5° C, agitated by a magnetic stirrer. Three-and-one-half gram portions of the powder blend were added and dissolution times were noted. Total dissolution was effected in 18 to 20 minutes.

EXAMPLE I-A

Comparative Example

The same test was run using 3.5 g of a blend of granular ingredients of the same composition, having the following screen analysis:

| Particle Size, U.S. Std. Sieve | Cumulative % Greater Than |
| --- | --- |
| 10 | 0.1 |
| 20 | 6.8 |
| 30 | 36.0 |
| 50 | 85.1 |
| 70 | 95.4 |
| 80 | 96.9 |
| 100 | 97.7 |
| −100 | 2.3 |

Total dissolution was effected in 50 minutes.

EXAMPLE II

Powder blends prepared as in Example I were partially hydrated by spraying water onto 150 g of the blend while it was being rotated in a small ball mill jar. Water added was 8.4% of the weight of the dry blend. Agglomeration was negligible, although a few soft lumps were formed. Dissolution tests were carried out as in Example I, and total dissolution time was again 18 to 20 minutes.

EXAMPLE III

Three-and-one-half gram portions of the powder blends, both anhydrous and partially hydrated as in Example II, were compacted into tablets of ¼ inch and ⅜ inch diameter. Tablets were pressed at 20,000 psi and 60,000 psi. Dissolution tests produced the following results:

| Composition | Pressed at, psi | Time of Pellet Disintegration | Time of Total Dissolution |
| --- | --- | --- | --- |
| Anhydrous | 20,000 | 9 min. | 19 min. |
| Anhydrous | 60,000 | 11 min. | 23 min. |
| 8.4% H$_2$O | 20,000 | 5.5 min. | 16 min. |
| 8.4% H$_2$O | 61,000 | 13 min. | 23 min. |

EXAMPLE IV

Tablets pressed from the anhydrous powder blend at 60,000 psi in Example III were crushed and screened to obtain a granular fraction of −10+70 mesh. When subjected to the dissolution test, 3.5 g of this material disintegrated in 3 minutes, and was completely dissolved in 20 minutes.

Examples I, II, III and IV show that anhydrous powder blends, partially hydrated blends, tablets of either type of powder blend, and coarse granules obtained by crushing and sizing tablets of powder blend dissolve in 16 to 23 minutes, which is ⅓ to ½ the 50 minutes required for a blend of granular ingredients to dissolve.

EXAMPLE V

A powder blend of 500 g was made in a laboratory roll mixer by mixing ingredients for 30 minutes in the following proportions: 41.8% of cyanuric acid, 49.1% of sodium dichloroisocyanurate dihydrate, and 9.1% of sodium carbonate. The cyanuric acid was of the same particle size as set forth in Example I. The sodium dichloroisocyanurate dihydrate was 0.5% maximum on 30 mesh (U.S. Standard Sieve), 5.0% maximum on 200 mesh. The sodium carbonate was Stauffer light ash, 0% on 40 mesh and 20% on 100 mesh, ground further in a mortar with a pestle. Fifteen-gram portions of this blend were compacted into tablets of 1⅛ inch diameter, under a pressure of 20,000 psi. The tablets were crushed and a −20+60 mesh fraction was separated by screening. Four grams of this material was introduced into 1,000 ml of distilled water at room temperature, magnetically stirred in a 1,500 ml beaker. Dissolution was completed in 22 minutes.

EXAMPLE V-A

Comparative Example

The dissolution test was also run using 4 g of a blend of granular ingredients of the same composition, having a particle size of −20+60 mesh. Total dissolution was effected in 65 minutes.

Again it is seen that the coarse granules obtained by crushing and sizing tablets of powder blend dissolve in ⅓ the time required for a blend of granular ingredients to dissolve.

Pursuant to the requirements of the patent statutes, the principal of this invention has been explained and exemplified in a manner so that it can be readily practiced by those skilled in the art, such exemplification including what is considered to represent the best embodiment of the invention. However, it should be clearly understood that, within the scope of the appended claims, the invention may be practiced by those skilled in the art, and having the benefit of this disclosure, otherwise than as specifically described and exemplified herein.

What is claimed is:

1. In the process of preparing a stabilized composition of matter containing as its essential components 10-70% of an alkali metal dichloroisocyanurate, 25-75% of cyanuric acid or the alkali metal salts thereof, and 5-50% of an inorganic salt, the pH of which is at least 9 and preferably 9-13 in aqueous media, the improvement of increasing the dissolution rate of said composition comprising (a) combining the ingredients in powder form to produce a homogeneous mixture; (b) compacting the homogeneous mixture under pressure and (c) crushing and screening the compacted materials of step (b) to provide a −10+70 mesh granular material.

2. The process of claim 1 in which the alkali metal dichloroisocyanurate in sodium dichloroisocyanurate dihydrate and the inorganic salt is sodium carbonate.

* * * * *